(12) United States Patent
Grossinger et al.

(10) Patent No.: US 7,508,508 B2
(45) Date of Patent: Mar. 24, 2009

(54) DEVICE AND METHOD FOR INSPECTING A HAIR SAMPLE

(75) Inventors: Israel Grossinger, Rechovot (IL);
Nadav Grossinger, Rechovot (IL);
Valery Shurman, Rishon-LeZion (IL)

(73) Assignee: SeeThrough Ltd., Nes Ziona (IL)

( * ) Notice: Subject to any disclaimer, the term of this patent is extended or adjusted under 35 U.S.C. 154(b) by 0 days.

(21) Appl. No.: 11/523,009

(22) Filed: Sep. 19, 2006

(65) Prior Publication Data
US 2008/0068604 A1 Mar. 20, 2008

(51) Int. Cl.
*G01J 3/28* (2006.01)
(52) U.S. Cl. ....................................... 356/328
(58) Field of Classification Search ................. 356/326, 356/328
See application file for complete search history.

(56) References Cited

U.S. PATENT DOCUMENTS

| 4,917,492 | A | * | 4/1990 | Koishi | 356/300 |
| 5,851,181 | A | * | 12/1998 | Talmor | 600/407 |
| 6,038,024 | A | | 3/2000 | Berner | |
| 6,707,929 | B2 | | 3/2004 | Marapane et al. | |
| 6,717,668 | B2 | * | 4/2004 | Treado et al. | 356/327 |
| 7,110,117 | B2 | | 9/2006 | Grossinger et al. | |
| 2004/0122782 | A1 | | 6/2004 | Audousset et al. | |
| 2005/0177032 | A1 | | 8/2005 | Grossinger et al. | |

FOREIGN PATENT DOCUMENTS

| EP | 0780671 | 6/1997 |
| GB | 2220479 | 1/1990 |

* cited by examiner

Primary Examiner—F. L Evans

(57) ABSTRACT

A device for inspecting a hair sample. The device comprises a measuring area configured to accommodate a hair sample and an imaging unit for receiving light flux reflected from the measuring area. The imaging unit outputs an image of the hair sample located in the measuring area. The device further comprises a spectral-analysis unit configured for receiving the light flux. The spectral-analysis unit outputs spectral analysis measurements of the hair sample according to the received light flux.

27 Claims, 5 Drawing Sheets

DEVICE AND METHOD FOR INSPECTING A HAIR SAMPLE

FIELD AND BACKGROUND OF THE INVENTION

The present invention relates to hair analysis and, more particularly but not exclusively, to a method and an apparatus for illuminating hair for analysis thereof.

Hair dyes and bleach are used to make gray hairs less conspicuous or to dye hair a desired color. Different types of hair dyes exist in the market. One example is a temporary hair dye, such as a color shampoo, a color conditioner, and a color treatment conditioner, which is easy to apply and remains for a short time. Another type of a hair dye is a semi-permanent dye, such as a dye that provides an effect that can be continuously maintained through penetration of an acidic dye into the interior of the hair. A commonly used hair dye is a permanent dye that achieves an essentially permanent dye effect through oxidative polymerization of the dye in the interior of the hair. A particular type of hair dye may be selected depending on the intended use.

Each of these types of dyes is prepared in numerous colors. Usually, a dye color is indicated on the box containing the dye, either by a color number or by means of a sample lock of dyed hair.

However, the color of the dye interacts with the color of the undyed hair. Thus, even where the same colored dye is used, the color of the hair after dyeing differs considerably depending on the natural color, or natural color plus old dye mixture of the hair before dyeing. For example, in a case where the hair before dyeing has a non homogenous mixture of white hair and colored hair, current methods fail to accurately predict the hair color after dyeing. Also, in a case where naturally pigmented hair is dyed with artificial colors, the resulting color depends on the combination of original and artificial pigments already present in the hair.

Consequently, it is difficult to predict the color that will result from dyeing any person's hair solely from the printing on a box or a sample lock of hair, and a problem often arises that the actual color of the hair after dyeing is different from the color anticipated.

Several methods and systems have been developed to predict the final hair color in order to minimize errors and increase customer satisfaction with the use of hair color products. For example, U.S. Pat. No. 6,707,929, filed on Mar. 16, 2004, describes a method and system for analyzing hair and predicting achievable dyed hair colors. The patent describes methods for identifying an achievable hair color based upon at least one starting hair value of a recipient, for identifying a hair coloring agent based upon at least one starting hair value of a recipient, and for outputting an image for a hair color analyzing system. The application further describes a method for providing a hair-coloring product to a consumer. The method comprises the steps of identifying achievable hair colors for the consumer, depicting the achievable colors to the consumer, allowing the consumer to select a desired hair color, and recommending to the consumer a hair-coloring agent to achieve the desired hair color. Another method and system for final hair color prediction is disclosed in U.S. patent application Ser. No. 10/345,249, entitled "Hair color measurement and treatment" to Grossinger, et al., filed on Oct. 1, 2003. This application introduces a system for measuring a reflectance spectrum of a hair sample. The system includes an integrating sphere having a sampling port and an inner surface and a window disposed near the sampling port. The window is placed in close contact with the sample. The system also includes a light source to project light onto the sample via the window and a light detector such as a spectrometer which analyzes light reflected from the inner surface to produce the reflectance spectrum of the sample.

The above methods and systems measure hair color using a spectral-analysis device that comprises a spectral sensor such as a colorimeter or a spectrometer. In use, the color measuring is done by analyzing the light which is reflected from a hair sample positioned in a measuring area in front of the spectral sensor. A light path has to be established between the device and the hair sample in order to ensure accurate measurement of the wavelength of the light which is reflected from the hair sample.

Apart from the light path between the spectral sensor and the hair sample, a light path for illuminating the hair sample has to be established. A considerable effort has been made to provide an accurate illumination subsystem in inspection system architectures that increase the intensity and quantity of light that is effectively available to illuminate image hair samples undergoing inspection. Such illumination subsystems usually comprise flashing units or arrays of light emitting diodes (LEDs), which are directed toward the measuring area. In use, the user of the spectral-analysis device has ensured that the hair sample of the client is in the probed measuring area and thus may wish to view the hair sample itself. The requirements to place the hair sample in the measuring area and to illuminate it may limit the arrangement of hair inspection systems. Moreover, some spectral-analysis devices have to be coupled to the head of the client in order to allow the positioning of the client's hair within the boundaries of the measuring area. In such devices, the user cannot see the hair he is measuring. Such an inability restricts the user's ability to verify that a particular hair sample is positioned in the measuring area and not a bald part of the scalp or another hair sample. This problem arises especially when the client has thinning hair and the positioning of the spectral-analysis device shifts part of the client's hair to outside the measuring area boundaries.

There is thus a widely recognized need for a system and a method that provides a hair inspection process that allows a user to verify whether or not a required hair sample is positioned within the measuring area. Additionally, it would be highly advantageous to have a hair inspection system and method devoid of the above limitations.

SUMMARY OF THE INVENTION

According to one aspect of the present invention there is provided a device for inspecting a hair sample. The device comprises a measuring area configured to accommodate a hair sample, an imaging unit for receiving light flux reflected from the measuring area, thereby outputting an image of the hair sample, and a spectral-analysis unit configured for receiving the light flux, therefrom to provide spectral analysis measurements of the hair sample.

Preferably, the device further comprises a path-diversion element configured for receiving the light flux and irradiating sensors respectively of the spectral-analysis unit and the imaging unit with the light flux.

More preferably, the path-diversion element is one member of the following group: a semi-transparent mirror, a rotating reflection mirror and a moving reflection mirror.

Preferably, the device further comprises light-emitting elements configured for emitting illumination light toward the measuring area.

Preferably, the light-emitting elements comprise at least one member of the group consisting of: a light emitting diode (LED), a white LED, a blue LED, a flashing light unit, and a bulb.

Preferably, the imaging unit comprises an image sensor configured for receiving the light flux.

More preferably, the image sensor comprises at least one member of the group consisting of: a charge coupled device (CCD) and a complementary metal oxide semiconductor (CMOS).

Preferably, the spectral-analysis unit comprises a spectral sensor configured for receiving and spectrally analyzing the light flux.

More preferably, the spectral-analysis unit comprises at least one member of the following group: an image sensor, an image sensor with a refraction grating and an array of spectral sensors.

More preferably, the respective irradiating of the sensors is done simultaneously.

More preferably, the respective irradiating of the sensors is done consecutively.

Preferably, the imaging unit further comprises a display component configured for displaying the image.

More preferably, the device further comprises a biconcave lens between the path-diversion element and the imaging unit, wherein the biconcave lens is configured for forming an image of the hair sample according to the light flux reflected onto an image forming plane of the imaging unit.

More preferably, the device further comprises a grating between the path-diversion element and the spectral-analysis unit, wherein the grating is configured for spreading the light flux onto an image forming plane of the spectral analysis unit.

According to another aspect of the present invention there is provided a device for inspecting a hair sample. The device comprises a spectral sensor, an image sensor, and a processing unit, associated with the sensors, configured for analyzing the hair sample by processing signals from the spectral sensor and configured for generating display signals according to the image sensor. The device further comprises a path-diversion element which is configured for receiving a reflection of light and irradiating both of the spectral analysis and image sensors with the reflection.

Preferably, the device further comprises light-emitting elements configured for emitting the light toward the hair sample.

Preferably, the path-diversion element is configured for splitting the reflection into reflected and transmitted light fluxes, the transmitted light flux being received by one of the spectral and image sensors, the reflected light flux being received by the other of the spectral and image sensors.

Preferably, the spectral sensor comprises at least one member of the following group: a spectral sensor, a colorimeter, a spectrometer, and a first image sensor.

Preferably, the image sensor comprises at least one member of the following group: a charge coupled device (CCD) and a complementary metal oxide semiconductor (CMOS).

Preferably, the path-diversion element is one member of the following group: a semi-transparent mirror, a rotating reflection mirror and a moving reflection mirror.

Preferably, the irradiating is done simultaneously.

Preferably, the irradiating is done consecutively.

More preferably, the light-emitting elements comprises at least one member of the following group: a light emitting diode (LED), a flashing light unit, and a bulb.

Preferably, the device further comprises a display unit configured for displaying an image according to the display signals.

More preferably, the device further comprises a biconcave lens between the path-diversion element and the image sensor, the biconcave lens being configured for forming an image of the hair sample according to the reflection on the image forming plane of the image sensor.

According to another aspect of the present invention there is provided a method for analyzing a hair sample. The method comprises the following steps:

a) Emitting light flux toward the hair sample.
b) Receiving a reflection of the light flux.
c) Diverting the reflection toward a plurality of sensors.
d) Analyzing properties of the hair sample according to outputs from at least one of the plurality of sensors.

Preferably, step (c) of diverting further comprises a step of splitting the reflection into reflected and transmitted light fluxes, the transmitted light flux being received by one of the plurality of sensors, the reflected light flux being received by at least one other of the plurality of sensors.

Preferably, step (d) further comprises a step of displaying an image of the hair sample according to outputs from at least one of the plurality of sensors.

Preferably, one of the plurality of sensors is a member of the following group: a spectral sensor, a colorimeter, a spectrometer, and an image sensor.

Preferably, step (d) further comprises a step of using the outputs for analysis of the wavelength of the reflection.

Preferably, one of the sensors is an image sensor.

More preferably, step (d) further comprises a step of using the outputs of the image sensor for generating an image of the hair sample.

Preferably, the step (c) of diverting further comprises simultaneously irradiating the plurality of sensors with the reflection.

Preferably, step (c) of diverting further comprises consecutively irradiating the plurality of sensors with the reflection.

Unless otherwise defined, all technical and scientific terms used herein have the same meaning as commonly understood by one of ordinary skill in the art to which this invention belongs. The materials, methods, and examples provided herein are illustrative only and are not intended to be limiting.

Implementation of the method and device of the present invention involves performing or completing certain selected tasks or steps manually, automatically, or a combination thereof. Moreover, according to actual instrumentation and equipment of preferred embodiments of the method and device of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and device of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
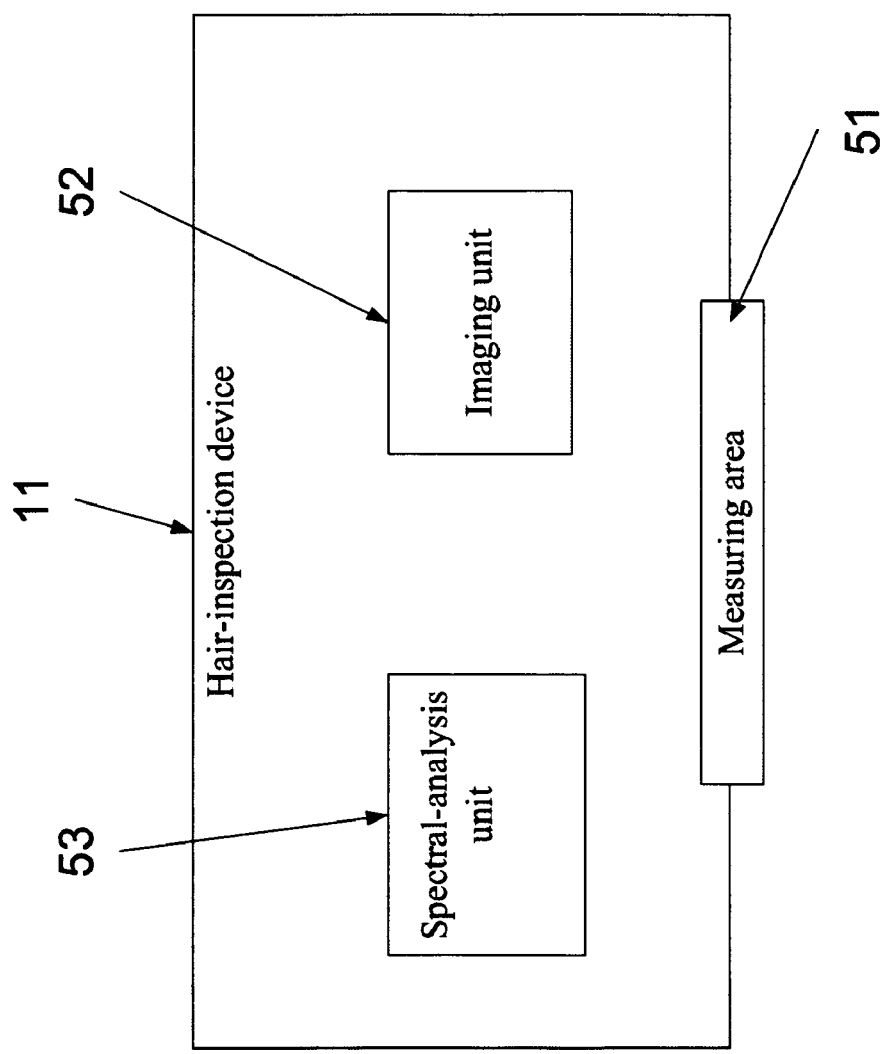
FIG. 1 is a schematic illustration of a device for analyzing hair samples having an imaging unit and a spectral-analysis unit, according to a preferred embodiment of the present invention.

The present embodiments comprise an apparatus and a method for analyzing a hair sample.

The principles and operation of an apparatus and method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. In addition, it is to be understood that the phraseology and terminology employed herein is for the purpose of description and should not be regarded as limiting.

In accordance with a general aspect of the invention there is provided a device that comprises two or more sensors which are simultaneously or consecutively employed. For example, one of the sensors is employed for inspecting a hair sample in a measuring area to obtain a spectral-analysis thereof, while another sensor is an image sensor for acquiring a two-dimensional image of the hair sample.

A preferred embodiment of the present invention is designed to provide a device for inspecting a hair sample. The device comprises a measuring area which is configured to accommodate a hair sample and an imaging unit for receiving light flux reflected from the measuring area. The device further comprises a spectral-analysis unit which is configured for receiving the light flux. While the imaging unit is configured for outputting an image of the hair sample according to the received light flux, the spectral-analysis unit is configured for outputting spectral-analysis measurements of the hair sample. The light flux, which is reflected from the hair sample, is received simultaneously or consecutively by the imaging and spectral-analysis units.

According to one embodiment of the present invention, there is provided a device for inspecting a hair sample. The device comprises two or more sensors such as an image sensor and a spectral sensor. The device further comprises a processing device, which is associated with one or more of the sensors. The processing device is used to analyze the hair sample by processing signals from one or more of the sensors. The device further comprises one or more light-emitting elements and a path-diversion element. The light-emitting elements are configured for emitting a light flux toward the hair sample, and the path-diversion element is configured for receiving a reflection of that light flux. The light-emitting elements are configured to simultaneously or consecutively irradiate the sensors with the reflection.

Another embodiment of the present invention is designed to provide a method for analyzing a hair sample. The method comprises several steps. During the first step, light flux is emitted toward the hair sample. Then a reflection of the light flux is received by a path-diversion element. In the following step, the path-diversion element diverts the reflection toward a number of sensors. The sensors output signals that represent the hair sample properties, according to the received reflections. These signals allow hair sample analysis to be performed, according to the hair sample properties.

Reference is now made to FIG. 1, which depicts a preferred hair-inspection device 11, having a measuring area 51 which holds a hair sample (not shown) and an imaging unit 52 which receives a reflection of light flux from the measuring area. The imaging unit 52 outputs an image of a hair sample in the measuring area. The hair-inspection device 11 includes a spectral-analysis unit 53 which also receives the reflection of the light flux and outputs spectral analysis measurements of the hair sample. As described below in further detail, the architecture of the device allows both the imaging unit 52 and the spectral-analysis unit 53 to simultaneously or consecutively receive light reflected from the hair sample.

Figure 2:
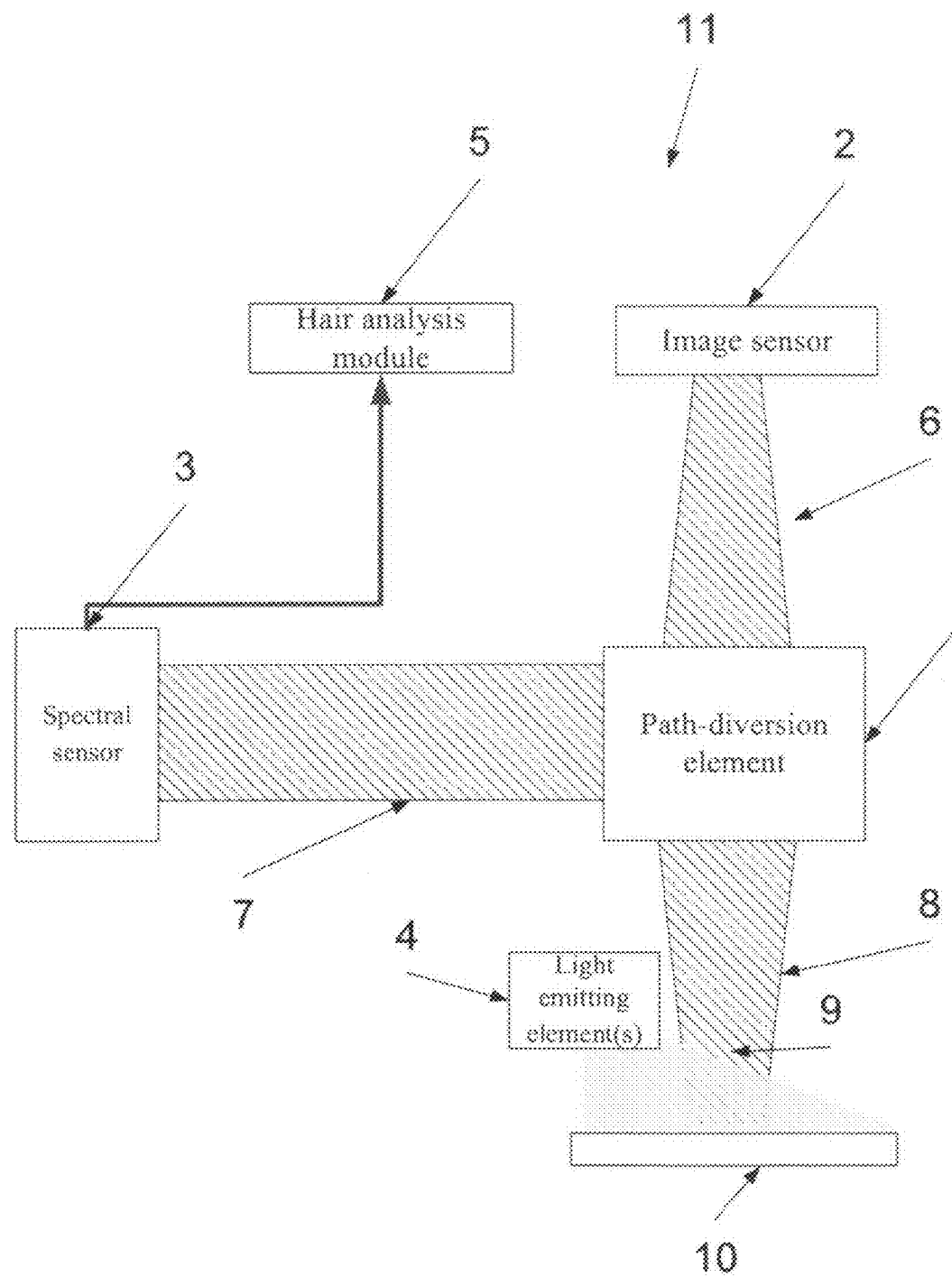
FIG. 2 is a schematic illustration of a device for analyzing hair samples using a path-diversion element, according to a preferred embodiment of the present invention.

Reference is now made to FIG. 2, which depicts a preferred embodiment of the hair-inspection device 11 shown in FIG. 1. In FIG. 2, the spectral-analysis unit (53 in FIG. 1) comprises a hair-analysis module 5, having a connection to a spectral sensor 3, and an image sensor 2. One or more light-emitting elements 4 emit light 9 toward a hair sample which is positioned in a predefined measuring area 10. A path-diversion element 1 is positioned to allow irradiating of both the sensors 2, 3 with light 8 reflected from the measuring area 10. Two alternatives of the path diversion element 1 will be described herein below. The sensors may be irradiated either simultaneously or consecutively. The light 8, which is reflected from the hair sample, is either diverted toward one or more of the sensors or is allowed to pass through the path-diversion element 1 toward one of the sensors.

The spectral sensor 3 of the spectral-analysis unit may be any sensor known in the art which is suitable for measuring the spectrum of the reflected from hair samples as a function of different wavelengths of light. Different sensors which are used to measure properties of light over a portion of the electromagnetic spectrum may be used. The measured variable may be the intensity of the light or the wavelength of the light.

It should be noted that the spectral sensor 3 may comprise an array of spectral sensors such as an array of optical sensors on a plane, etc. Such arrays may offer a wider variety of spectral measurement ranges and better resolution. Preferably, the spectral sensor 3 is an array of co-aligned reflection gratings and an array of back-illuminated CCD detectors that detect the light reflected and dispersed by the reflection-grating array. For example, U.S. patent application Ser. No. 10/473,627, entitled "Hair Color Measurement and Treatment," to Grossinger, et al., filed on Oct. 1, 2003, which is hereby incorporated by reference, introduces a spectrometer for producing a usable reflectance spectrum of hair without having to remove the hair sample from the head of the customer.

As depicted in FIG. 2, the spectral sensor 3 is connected to a hair-analysis module 5. The hair-analysis module 5 may be configured to predict a spectrum of hair mixtures resulting from applying a plurality of dye colors to a hair mixture. For example, U.S. patent application Ser. No. 11/328,337, entitled "Method for Analyzing Hair," to Grossinger, et al., filed on Jan. 10, 2006, which is hereby incorporated by reference, introduces a hair-analysis module that predicts the spectrum of a hair mixture resulting from applying a dye color. Preferably, the predicted spectrum may be visually presented to a client prior to dyeing his hair, so as to provide an image representative of his hair color after dyeing with the dye color. The spectrum predication of the hair-analysis module 5 is based on measurements of the absorption and attenuation in the hair sample, as captured by the spectral sensor 3.

The spectral sensor 3 is configured to analyze light reflected from a hair sample in order to produce a reflectance spectrum thereof. Thus, a source of light has to be integrated into the device in order to project light that can be reflected from the hair sample onto the spectral sensor 3.

As shown in FIG. 2, light-emitting elements 4 project light onto the hair sample, as shown at 9, preferably via a window (not shown). Thus, the hair sample has to be positioned in a manner that allows the spectral sensor 3 to receive light reflected therefrom. Light 8 is then reflected off of the hair sample onto the path-diversion element 1 of the hair-inspection device 11. Light-emitting elements such as light emitting diodes (LEDs), flashing units, and bulbs may be used for projecting light 9 onto the hair sample. Different kinds of LEDs such as red, blue or white LEDs may be used.

As noted above, the imaging unit comprises an image sensor 2. The imaging unit preferably comprises a computing unit (not shown) which receives in real time digital images from the image sensor 2, via a designated image input module (not shown). As depicted in FIG. 2, light 8 which is reflected off of a hair sample onto the path-diversion element 1 may be diverted toward the image sensor 2. The image sensor 2 is configured to convert the received reflection 6 into electrical signals. The signals are forwarded to the computing unit. The image sensor 2 is preferably a complementary metal oxide semiconductor (CMOS) sensor or a charge coupled device (CCD) sensor. When such image sensors are used, the light 8 which is reflected off of a hair sample onto the path-diversion element 1 is diverted toward the image forming plane of the image sensor 8.

Preferably, the hair-analysis module 5 is connected to a display unit (not shown) that receives electrical signals and, accordingly, generates a display of the hair sample which is positioned in the measuring area 10. The display unit allows the hair being measured to be shown next to its spectrum or next to the calculated dye application results. The display unit allows a user can target a specific hair sample he wants to analyze. As the image sensor generates images according to light reflected from the measuring area, such an embodiment ensures that the spectral sensor 3 receives the same light reflected from the hair sample which is displayed on the display unit. The user can use the display to verify that a particular hair sample that is suitable for the spectral analysis is positioned in the measuring area 10 and not a bald part of the scalp or another hair sample.

Figure 3:
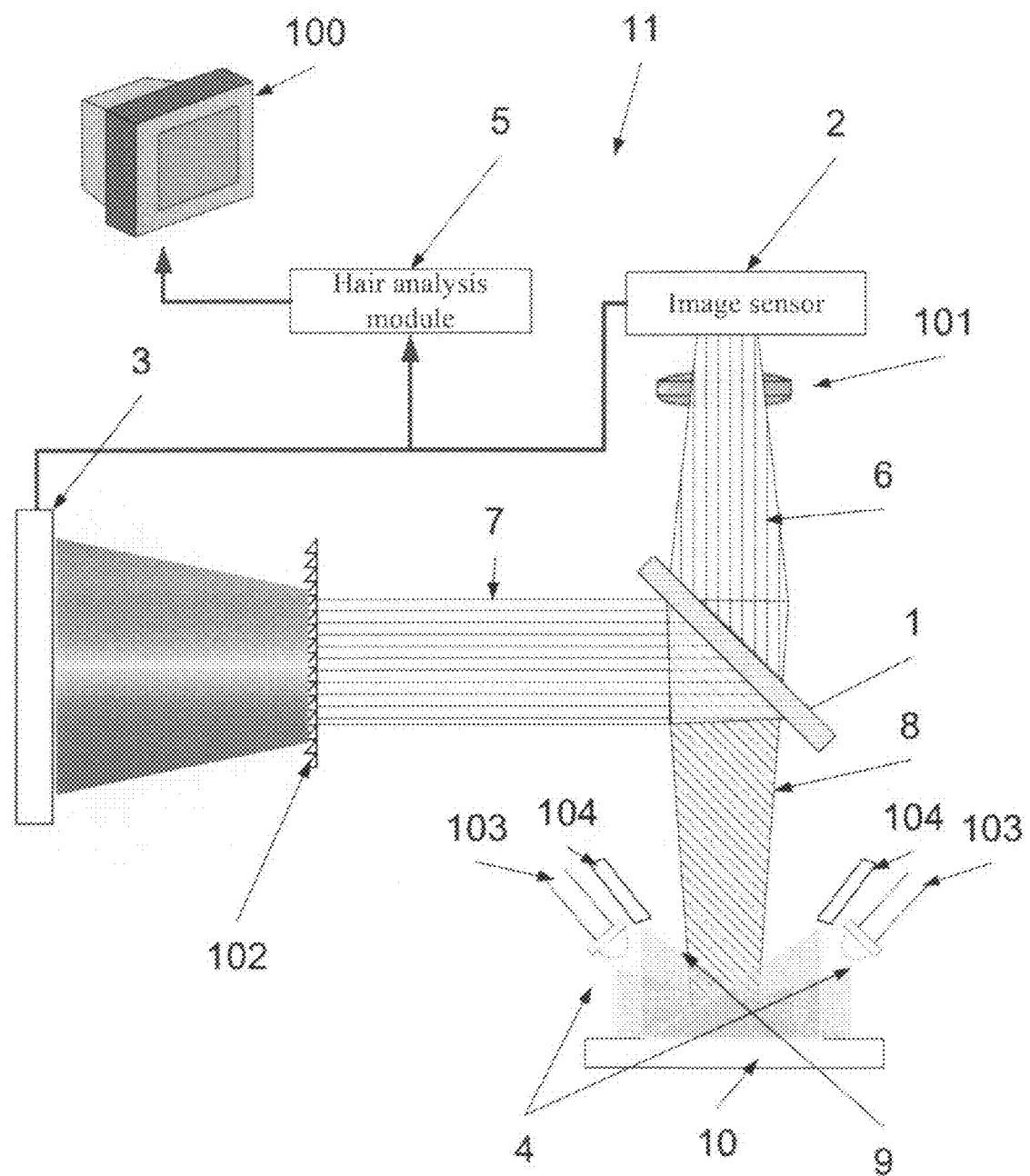
FIG. 3 is a schematic illustration of a device for analyzing hair samples using a semi-transparent mirror, according to an embodiment of the present invention.

Reference is now made to FIG. 3, which is a perspective view of a hair-inspection device 11 in which the path-diversion element 1 is a semi-transparent mirror, according to a preferred embodiment of the present invention. In this embodiment, all the components of the hair-inspection device 11 are the same as in FIG. 2. In FIG. 3, however, the hair-inspection device 11 further comprises a biconcave lens 101 and a grating 102. Moreover, with regard to FIG. 3, there is a more elaborate description of the light emitting elements 4.

As described above, the path-diversion element 1 is used for conveying the light flux 8 reflected from the hair sample to two or more sensors 2 and 3. In FIG. 3, the semi-transparent mirror 1 is used to divide the light flux 8, so that a first portion 6 of the light flux is directed onto the image sensor 2 and a second portion 7 of the light flux is directed onto the spectral sensor 3. The first portion 6 of the light flux passes through the semi-transparent mirror 1, while the second portion 7 of the light flux is diverted by the semi-transparent mirror 1 onto the spectral sensor 3.

Preferably, the biconcave lens 101 is used to expand the first portion 6 of the light flux and to increase it focal length before it is projected onto the image sensor 2.

Preferably, the grating 102 is used for dispersing the second portion 7 of the light flux into its constituent spectral colors. Such a grating improves the accuracy of the spectral sensor 3.

The hair-inspection device 11, which is depicted in FIG. 3, allows the analysis of a hair sample and the simultaneous displaying thereof. As described above, the spectral sensor 3 is used for estimating the reflectance spectrum of the hair sample and for forwarding the estimation to the hair-analysis module 5 that predicts the spectrum of the final hair mixture resulting upon applying different dye colors to the hair mixture. The image sensor 2 is configured to transmit digital images to a computing unit (not shown) of the imaging unit that instructs a display unit 100 to display an image of the hair sample, as described above.

In another embodiment (not shown) of the present invention, the image and the spectral sensors are affixed to rotating or shifting mountings. Such mountings are configured to allow the reflected light 8 to irradiate the image sensor and the spectral sensor in a sequential manner. Preferably, the rotating mountings are spun at substantially constant rates, preferably by an electric motor assembly, or at variable rates, according to the user configuration, preferably by a servomotor assembly.

Figure 4:
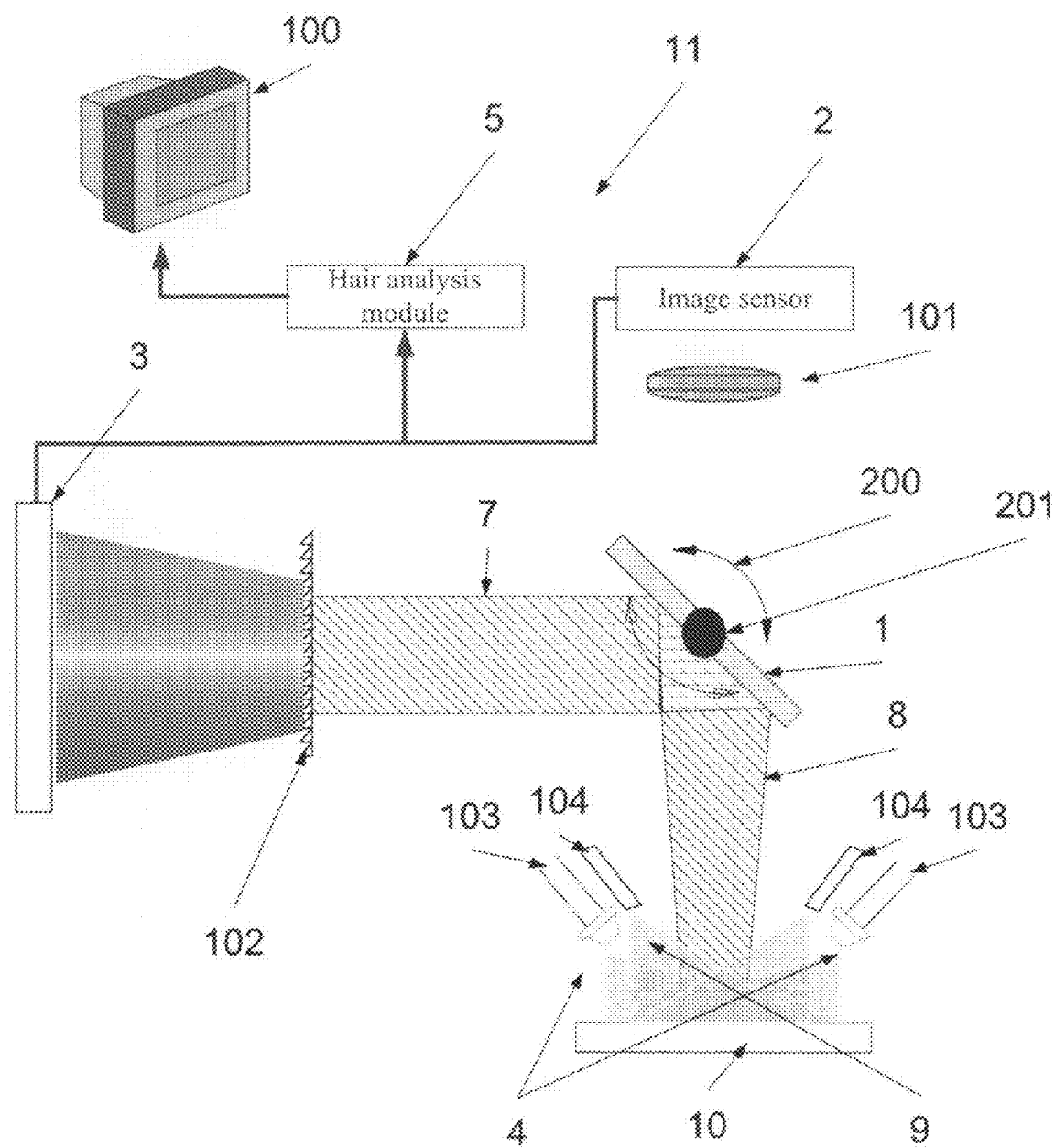
FIG. 4 is a schematic illustration of a device for analyzing hair samples using a rotatable mirror, according to an embodiment of the present invention.

Reference is now made to FIG. 4, which is a perspective view of a hair-inspection device 11 in which the path-diversion element 1 is a moving mirror module, according to another embodiment of the present invention. The moving mirror module comprises a rotatable mirror or a shiftable mirror and an actuation mechanism for rotating or shifting the mirror. In the embodiment shown, apart from the path-diversion element 1, all the components of the hair-inspection device 11 are the same as those in FIG. 3. In FIG. 4, the moving mirror module comprises a rotatable mirror 1 which is configured to divert light 8, which is reflected from the hair sample, either to the spectral sensor 3 or to the image sensor 2, according to the rotational angle 200 of the rotatable mirror 1.

The rotatable mirror 1 of FIG. 4 is affixed to a rotating mounting 201, which is preferably spun at a substantially constant rate (for example, 600-1200 RPM), preferably by an electric motor assembly, or at a variable rate, according to the user configuration, preferably by a servomotor assembly. It should be noted that more than two image sensors may be radiated by the rotatable mirror, as the light may be reflected according to the rotational angle of the rotatable mirror to more than two rotational angles. In such an embodiment, the rotatable mirror is rotated to more than two positions, one for the image sensor and others for the spectral sensors.

Different actuating mechanisms may be used for rotating the rotatable mirror. For example, a simple belt and pulley arrangement may be used to drive a flanged wheel formed integrally with the base of the rotating mounting 201. Various alternative equivalent rotation means will readily become apparent to persons of ordinary skill in the art.

The rotational angle 200 of the rotatable mirror may be correlated with the light-emitting element 4. Each of FIGS. 3 and 4 depicts an exemplary multiphase light-emitting element 4. As described above, the rotatable mirror 1 is used for diverting the light 8, which is reflected from the hair sample to both the image sensor 2 and the spectral sensor 3. However, these sensors may require different illumination levels in the measuring area 10 that comprises the hair sample. The multiphase light-emitting element 4, which is depicted in FIG. 4, integrates both LEDs 103 and flashing units 104. Preferably, while the LEDs are used for illuminating the hair sample for the usage of both the image sensor 2 and the spectral sensor 3, the flashing units 104 are activated only for illuminating the hair sample when the spectral sensor 3 is activated. By adjusting the multiphase light-emitting element 4 to different phases of the device, images, which are taken by using the image sensor 2, are not constantly exposed to the excessive illumination of the flashing unit 104 that may saturate the image's pixels so that a captured hair sample may become difficult to differentiate. Such an embodiment ensures that, during the spectral-analysis it, sufficient light is reflected to be captured by the spectral sensor 3 and when the spectral-analysis process is idle, images can be captured without illumination by the flashing units 104. Nevertheless the two processes can be carried out simultaneously on the same sample. It should be noted that by activating the flashing units 104 only when needed, as described above, electricity and bulb replacement are saved. As relatively expensive and sensitive components such as white LEDs may comprise the flashing units 104, such a manageable activation of the multiphase light-emitting element 4 contributes to the robustness and economization of the system.

Figure 5:
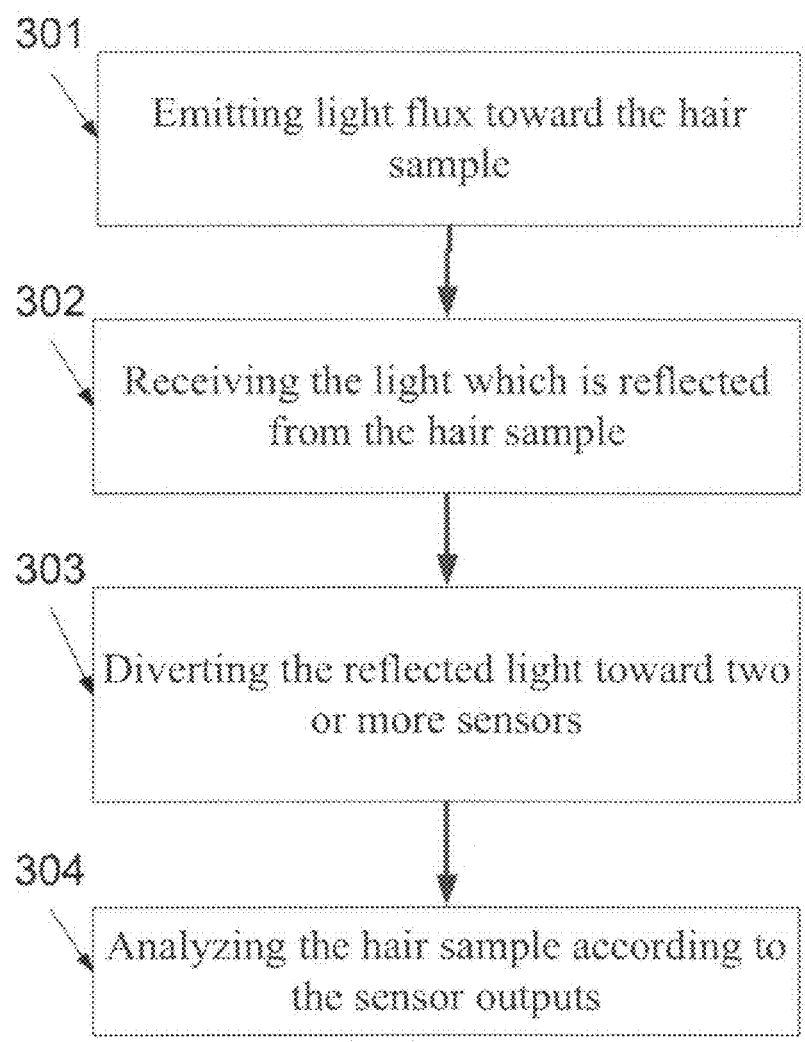
FIG. 5 is a flowchart of a method for analyzing a hair sample, according to a preferred embodiment of the present invention.

Reference is now made to FIG. 5, which is a flowchart that illustrates a method for analyzing a hair sample, according to a preferred embodiment of the present invention. FIG. 5 depicts a four-step process, which allows two or more sensors to simultaneously or consecutively receive light that is reflected from a probed hair sample.

The depicted method may be implemented in various hair analyzing devices that integrate two or more light sensors. In one embodiment of the present invention, the user of the hair-analyzing device may push a designated button or other man-machine interface (MMI) control in order to initiate the implementation of the method steps. During the first step, 301, light is emitted toward a probed hair sample. The light flux is emitted from light-emitting elements, as described above. In the following step, 302, the light, which is reflected from the hair sample, is received by a path-diversion element, such as a semi-transparent mirror or a rotatable mirror. The path-diversion element is used for diverting the reflected light toward two or more sensors, as shown at 303. In one embodiment of the present invention, a semi-transparent mirror is used for splitting the received reflection into transmitted and reflected fluxes. While the transmitted light flux irradiates an image sensor, the reflected light flux irradiates a spectral sensor. In another embodiment of the present invention, a rotatable mirror is used to divert the reflected light flux in a sequential manner toward the spectral sensor and the image sensor. In the following step, 304, outputs from one or more of the sensors are used for analyzing the properties of the hair sample. Such properties may include the reflectance spectrum of the hair sample.

It is expected that during the life of this patent many relevant devices and systems will be developed and the scope of the terms herein, particularly of the terms sensor, spectral sensor, rotatable mirror, and semi-transparent mirror is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device for inspecting a hair sample, said device comprising:
 a measuring area configured to accommodate a hair sample;
 an imaging unit configured over a first light path, for receiving light flux reflected from said measuring area, thereby outputting an image of said hair sample; and
 a spectral-analysis unit configured over a second light path, for receiving said light flux, therefrom to provide spectral analysis measurements of said hair sample, said first and second light paths being configured with a light switch such that each light path is used consecutively in alternating manner.

2. The device of claim 1, further comprising a path-diversion element configured for receiving said light flux and irradiating sensors respectively of said spectral-analysis unit and said imaging unit with said light flux.

3. The device of claim 2, wherein said path-diversion element is one member of the following group: a rotating reflection mirror and a moving reflection mirror.

4. The device of claim 1, further comprising at least one light-emitting element configured for emitting illumination light toward said measuring area.

5. The device of claim 4, wherein said at least one light-emitting element comprises at least one member of the group consisting of: a light emitting diode (LED), a white LED, a blue LED, a flashing light unit, and a bulb.

6. The device of claim 1, wherein said imaging unit comprises an image sensor configured for receiving said light flux.

7. The device of claim 6, wherein said image sensor comprises at least one member of the group consisting of: a charge coupled device (CCD) and a complementary metal oxide semiconductor (CMOS).

8. The device of claim 1, wherein said spectral-analysis unit comprises a spectral sensor configured for receiving and spectrally analyzing said light flux.

9. The device of claim 8, wherein said spectral-analysis unit comprises at least one member of the following group: an image sensor, an image sensor with a refraction grating and an array of spectral sensors.

10. The device of claim 1, wherein said imaging unit further comprises a display component configured for displaying said image.

11. The device of claim 2, further comprising a biconcave lens between said path-diversion element and said imaging unit, wherein said biconcave lens is configured for forming an image of said hair sample according to said light flux reflected onto an image forming plane of said imaging unit.

12. The device of claim 2, further comprising a grating between said path-diversion element and said spectral-analysis unit, wherein said grating is configured for spreading said light flux onto an image forming plane of said spectral analysis unit.

13. A device for inspecting a hair sample, said device comprising:
    a spectral sensor;
    an image sensor;
    a processing unit, associated with said sensors, configured for analyzing said hair sample by processing signals from said spectral sensor and configured for generating display signals according to said image sensor; and
    a path-diversion element configured for receiving a reflection of light and irradiating both of said spectral analysis and image sensors consecutively in alternating manner with said reflection.

14. The device of claim 13, further comprising at least one light-emitting element configured for emitting said light toward said hair sample.

15. The device of claim 13, wherein said spectral sensor comprises at least one member of the following group: a spectral sensor, a colorimeter, a spectrometer, and a first image sensor.

16. The device of claim 13, wherein said image sensor comprises at least one member of the following group: a charge coupled device (CCD) and a complementary metal oxide semiconductor (CMOS).

17. The device of claim 13, wherein said path-diversion element is one member of the following group: a rotating reflection mirror and a moving reflection mirror.

18. The device of claim 14, wherein said at least one light-emitting element comprises at least one member of the following group: a light emitting diode (LED), a flashing light unit, and a bulb.

19. The device of claim 13, further comprising a display unit configured for displaying an image according to said display signals.

20. The device of claim 16, further comprising a biconcave lens between said path-diversion element and said image sensor, said biconcave lens being configured for forming an image of said hair sample according to said reflection on the image forming plane of said image sensor.

21. A method for analyzing a hair sample, said method comprising:
    a) emitting light flux toward said hair sample;
    b) receiving a reflection of said light flux;
    c) diverting said reflection consecutively in alternating manner toward a plurality of sensors; and
    d) analyzing properties of said hair sample according to outputs from at least one of said plurality of sensors.

22. The method of claim 21, wherein said step (d) further comprises a step of displaying an image of said hair sample according to outputs from at least one of said plurality of sensors.

23. The method of claim 21, wherein one of said plurality of sensors is a member of the following group: a spectral sensor, a colorimeter, a spectrometer, and an image sensor.

24. The method of claim 23, wherein said step (d) further comprises a step of using said outputs for analysis of the wavelength of said reflection.

25. The method of claim 21, wherein one of said sensors is an image sensor.

26. The method of claim 25, wherein said step (d) further comprises a step of using the outputs of said image sensor for generating an image of said hair sample.

27. The method of claim 21, wherein said step (c) of diverting further comprises consecutively irradiating said plurality of sensors with said reflection.

* * * * *